US012636096B2

(12) United States Patent (10) Patent No.: US 12,636,096 B2
Meglan et al. (45) Date of Patent: May 26, 2026

(54) SYSTEM AND METHOD FOR INTEGRATED CONTROL OF 3D VISUALIZATION THROUGH A SURGICAL ROBOTIC SYSTEM

(71) Applicant: Covidien LP, Mansfield, MA (US)

(72) Inventors: Dwight Meglan, Westwood, MA (US);
Meir Rosenberg, Newton, MA (US);
Robert W. Pierce, Franklin, MA (US)

(73) Assignee: Covidien LP, Mansfield, MA (US)

( * ) Notice: Subject to any disclaimer, the term of this patent is extended or adjusted under 35 U.S.C. 154(b) by 224 days.

(21) Appl. No.: 17/922,824

(22) PCT Filed: May 24, 2021

(86) PCT No.: PCT/US2021/033862
§ 371 (c)(1),
(2) Date: Nov. 2, 2022

(87) PCT Pub. No.: WO2021/242681
PCT Pub. Date: Dec. 2, 2021

(65) Prior Publication Data
US 2023/0172674 A1 Jun. 8, 2023

Related U.S. Application Data

(60) Provisional application No. 63/031,709, filed on May 29, 2020.

(51) Int. Cl.
*A61B 34/30* (2016.01)
*A61B 34/10* (2016.01)
(Continued)

(52) U.S. Cl.
CPC .............. *A61B 34/30* (2016.02); *A61B 34/10* (2016.02); *G06T 7/33* (2017.01); *G06T 19/20* (2013.01);
(Continued)

(58) Field of Classification Search
CPC ......... A61B 34/10; A61B 34/25; A61B 34/30; A61B 34/37; A61B 2034/105;
(Continued)

(56) References Cited

U.S. PATENT DOCUMENTS

2006/0293557 A1 12/2006 Chuanggui et al.
2016/0324580 A1 11/2016 Esterberg
(Continued)

FOREIGN PATENT DOCUMENTS

CN 108289600 A 7/2018
CN 109785374 A 5/2019
(Continued)

OTHER PUBLICATIONS

International Search Report and Written Opinion of the International Searching Authority issued in corresponding application PCT/US2021/033862 mailed Sep. 2, 2021 (14 pages).
(Continued)

*Primary Examiner* — Jason Holloway
*Assistant Examiner* — Blake A Wood
(74) *Attorney, Agent, or Firm* — Carter, DeLuca & Farrell, LLP

(57) ABSTRACT

A surgical robotic system includes a control tower, a mobile cart, and a surgical console. The mobile cart is coupled to the control tower and includes a surgical robotic arm. The surgical robotic arm includes a surgical instrument and an image capture device. The surgical instrument is actuatable in response to a user input and configured to treat a target tissue in real-time. The image capture device for capturing at least one of images or video of the target tissue in real-time. The surgical console includes a user input device for generating a user input, and a controller. The controller is operably coupled to the user input device and configured
(Continued)

to switch, based on the user input, from a first mode to a second mode, and from the second mode to the first mode.

20 Claims, 9 Drawing Sheets

(51) Int. Cl.
*G06T 7/33* (2017.01)
*G06T 19/20* (2011.01)

(52) U.S. Cl.
CPC ..... *A61B 2034/105* (2016.02); *G06T 2200/24* (2013.01); *G06T 2207/10021* (2013.01)

(58) Field of Classification Search
CPC ...... A61B 2034/107; A61B 2034/2065; A61B 2090/064; G06T 7/33; G06T 19/006; G06T 19/20; G06T 2200/24; G06T 2207/10016; G06T 2207/10021; G06T 2210/41; G06T 2219/2016
See application file for complete search history.

(56) References Cited

U.S. PATENT DOCUMENTS

| | | | | |
|---|---|---|---|---|
| 2018/0042680 | A1* | 2/2018 | DiMaio | G16H 20/40 |
| 2018/0092706 | A1 | 4/2018 | Anderson et al. | |
| 2018/0368930 | A1* | 12/2018 | Esterberg | G06T 17/00 |
| 2019/0159699 | A1* | 5/2019 | Coste-Maniere | G06T 7/60 |
| 2019/0159848 | A1* | 5/2019 | Quaid | A61B 34/37 |
| 2019/0231456 | A1 | 8/2019 | Ruiz et al. | |
| 2019/0254754 | A1* | 8/2019 | Johnson | G06T 19/006 |
| 2020/0013224 | A1 | 1/2020 | Cvetko et al. | |
| 2020/0038124 | A1 | 2/2020 | Lin et al. | |
| 2020/0138534 | A1 | 5/2020 | Garcia Kilroy et al. | |
| 2021/0065451 | A1* | 3/2021 | Tseng | G06T 7/73 |
| 2021/0121237 | A1* | 4/2021 | Fanson | A61B 34/20 |
| 2021/0169578 | A1* | 6/2021 | Calloway | A61B 90/37 |

FOREIGN PATENT DOCUMENTS

| | | |
|---|---|---|
| CN | 110010249 A | 7/2019 |
| GB | 2577719 A | 4/2020 |
| WO | 2019083805 A1 | 5/2019 |
| WO | 2019139949 A1 | 7/2019 |

OTHER PUBLICATIONS

Office Action issued in corresponding Chinese application 202180037851.1 dated Jun. 16, 2025, together with English language translation.

Communication Pursuant to Article 94(3) EPC issued in corresponding EP 21 729 782.9 dated Jan. 12, 2026, 13 pages.

* cited by examiner

SYSTEM AND METHOD FOR INTEGRATED CONTROL OF 3D VISUALIZATION THROUGH A SURGICAL ROBOTIC SYSTEM

CROSS REFERENCE TO RELATED APPLICATIONS

The present application is a National Stage Application under 35 U.S.C. § 371(a) of PCT/US2021/033862, filed May 24, 2021, which claims the benefit of and priority to U.S. Patent Provisional Application No. 63/031,709 filed on May 29, 2020. The entire disclosures of the foregoing applications are incorporated by reference herein.

FIELD

The present disclosure is generally related to a robotic surgical system, in particular, a system and method for integrated control of a surgical robotic system and 3D visualization of a surgical site to register the 3D model with a target tissue in the surgical site.

BACKGROUND

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm.

Typically, during surgical procedures with the surgical robotic system the clinician utilizes 3D models of a surgical site to develop a surgical plan. In most cases, the clinician would display the 3D model on a separate interactive display. This requires the clinician to switch from the surgical robotic system controls to a separate control to interact with the 3D model on the separate interactive display thereby distracting the clinician.

SUMMARY

This disclosure generally relates to a surgical robotic system including a user interface controller for providing integrated control of a 3D model through the controls of the surgical robotic system to register the 3D model with a target tissue of the surgical site.

In one aspect, the present disclosure provides a surgical robotic system including a control tower, a mobile cart, and a surgical console. The mobile cart is coupled to the control tower and includes a surgical robotic arm. The surgical robotic arm includes a surgical instrument and an image capture device. The surgical instrument is actuatable in response to a user input and configured to treat a target tissue in real-time. The image capture device is configured to capture at least one of images or video of the target tissue in real-time. The surgical console is coupled to the control tower and includes a display, a memory, a user input device, and a controller. The memory is configured to store pre-operative images of the target tissue. The user input device is configured to generate the user input. The controller is operably coupled to the display, the memory, and the user input device and configured to switch, based on the user input, from a first mode to a second mode, and from the second mode to the first mode. The first mode includes displaying the target tissue in real-time and activating control of the surgical robotic arm by the user input device and the second mode includes displaying a 3D model of the target tissue and activating interactive control of the 3D model of the target tissue by the user input device.

In aspects, the surgical console may further include an image processor configured to display or generate the 3D model of the target tissue based on the stored pre-operative images of the target tissue at the surgical site In aspects, the interactive control of the 3D model of the target tissue may include adjusting at least one of scale, position, orientation of the 3D model of the target tissue or at least one heuristic factor.

In aspects, the controller may be further configured to maintain or retain an actual position of the user input device from the first mode.

In aspects, the controller may be further configured to determine a desired position of the user input device by sensing a directional force on the user input device.

In aspects, the controller may be further configured to analyze the surface of the target tissue in real-time.

In aspects, the controller may be further configured to determine at least one of tissue property, mechanical property, shape, fiducial markings of the target tissue or heuristic factors.

In aspects, the controller may be further configured to manipulate the 3D model of the target tissue based on the determined at least one of tissue property, mechanical property, shape, fiducial markings of the target tissue in real-time or heuristic factors to further register the 3D model of the target tissue with the target tissue in real-time.

In aspects, the controller may be further configured to determine completion of registration of the 3D model of the target tissue with the target tissue in real-time.

In aspects, the controller may be further configured to superimpose the 3D model of the target tissue over the target tissue in real-time, based on the completion of registration of the 3D model of the target tissue with the target tissue in real-time.

In aspects, the controller may be further configured to synchronize at least one of a position or orientation of the image capture device with a viewpoint of the 3D model of the target tissue.

In another aspect, the disclosure provides a method of registering a 3D model of a target tissue with a real-time image of the target tissue via a user input device of a surgical robotic system. The method includes generating or displaying a 3D model of a target tissue based on stored pre-operative images of the target tissue; capturing, by an image capture device, at least one of images or video of the target tissue in real-time; activating a first mode to display the target tissue in real-time and treating the target tissue in response to a user input device; switching from the first mode to a second mode to display the 3D model of the target tissue; manipulating the 3D model of the target tissue, via the user input device, to register the 3D model of the target tissue with the target tissue in real-time; and switching from the second mode to the first mode to further register the 3D model of the target tissue with the target tissue in real-time.

In aspects, manipulating the 3D model of the target tissue to register the 3D model of the target tissue with the target tissue in real-time may include activating interactive control of the 3D model of the target tissue via the user input device.

In aspects, the interactive control of the 3D model of the target tissue may include adjusting at least one of scale, position, orientation of the 3D model of the target tissue or at least one heuristic factor.

In aspects, switching from the first mode to the second mode may include maintaining an actual position of the user input device and sensing a directional force on the user input device to determine a desired position of the user input device.

In aspects, switching from the second mode to the first mode to further register the 3D model of the target tissue with the target tissue may include analyzing the surface of the target tissue in real-time.

In aspects, analyzing the surface of the target tissue in real-time may include determining at least one of tissue property, mechanical property, shape, fiducial markings of the target tissue in real-time or heuristic factors.

In aspects, determining the at least one of tissue property, mechanical property, shape or fiducial markings of the target tissue in real-time may include manipulating the 3D model of the target tissue based on the determined at least one of tissue property, mechanical property, shape, fiducial markings of the target tissue in real-time or heuristic factors.

In aspects, the method may further include determining completion of registration of the 3D model of the target tissue with the target tissue in real-time; and superimposing the 3D model of the target tissue over the target tissue in real-time, based on the completion of the registration of the 3D model of the target tissue with the target tissue in real-time.

In aspects, the method may further include synchronizing at least one of a position or orientation of the image capture device with a viewpoint of the 3D model of the target tissue.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
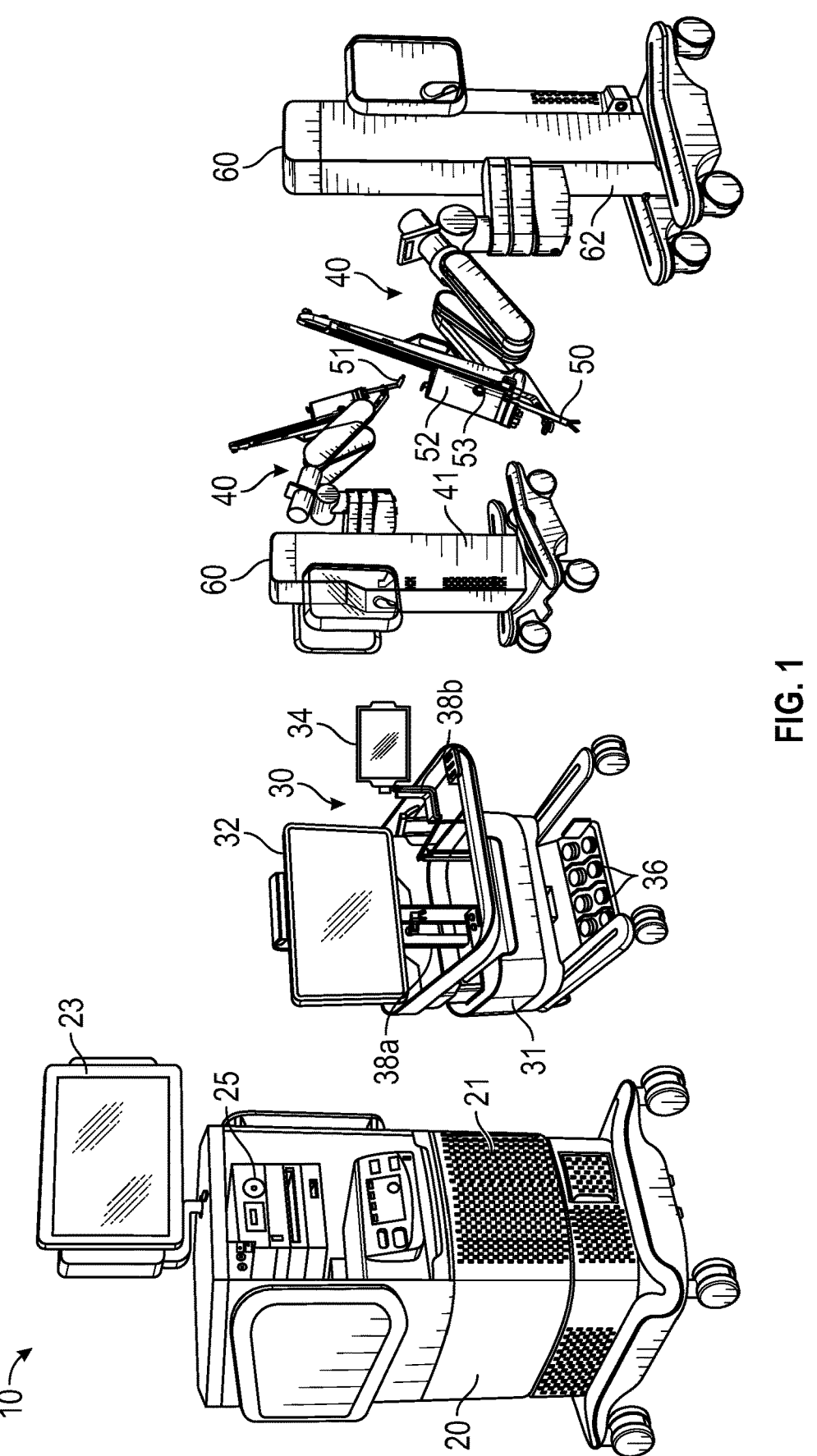
FIG. 1 is a schematic illustration of a surgical robotic system including a control tower, a console, and one or more surgical robotic arms in accordance with aspects of the present disclosure.

The presently disclosed surgical robotic systems are described in detail with reference to the drawings, in which like reference numerals designate identical or corresponding elements in each of the several views.

As will be described in detail below, the present disclosure is directed to a surgical robotic system which includes a surgical console, a control tower, and one or more movable carts having a surgical robotic arm coupled to a setup arm. The surgical console is configured to select, by a user input device of the surgical console, between a first mode and a second mode and activate control of the robotic surgical arms or a display of the surgical console, based on the user input. The clinician controls either the robotic surgical arms or the display of the surgical console.

The term "application" may include a computer program designed to perform functions, tasks, or activities for the benefit of a clinician. Application may refer to, for example, software running locally or remotely, as a standalone program or in a web browser, or other software which would be understood by one skilled in the art to be an application. An application may run on a controller or a user device, including, for example, a mobile device, an IOT device, or a server system.

The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), Ethernet/EtherCat, and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. Alternatively, the surgical instrument 50 may be configured for open surgical procedures. In aspects, the surgical instrument 50 may be an endoscope configured to provide a video feed for the user, may be an electrosurgical forceps configured to seal tissue by compression tissue between jaw members and applying electrosurgical current thereto, or may be a surgical stapler including a pair of jaws configured to grasp and clamp tissue whilst deploying a plurality of tissue fasteners, e.g., staples, and cutting stapled tissue.

Figure 6:
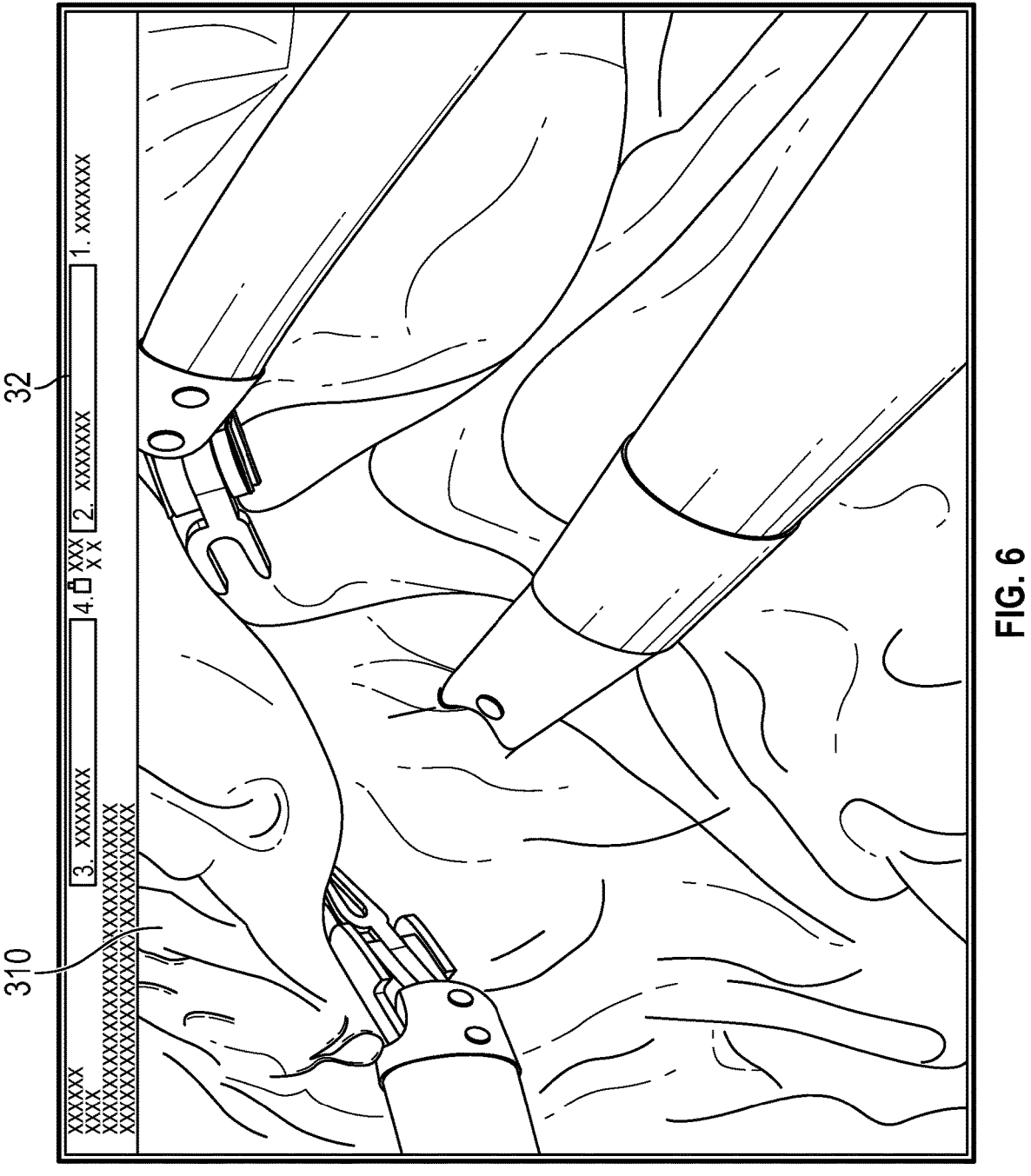
FIG. 6 is an exemplary view of a display of a target tissue at a surgical site, in a first mode.

Each of the robotic arms 40 may include an input capture device or camera 51 configured to capture video of a surgical site 310 (FIG. 6). The camera 51 may be a stereoscopic camera and may be disposed on the robotic arm 40. The surgical console 30 includes a first display 32, which displays a video feed of the surgical site 310 (FIG. 6) provided by camera 51 disposed on the robotic arms 40, and a second display device 34, which displays a user interface for controlling the surgical robotic system 10. The surgical console 30 also includes a plurality of user interface devices, such as foot pedals 36 and a pair of handle controllers 38a and 38*b* which are used by a user to remotely control robotic arms 40, e.g., a teleoperation of the robotic arms 40 via the surgical console.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38*a* and 38*b*. In some instances, the control tower 20 may not be included in the surgical robotic system 10, instead the control tower 20 of the surgical robotic system 10 may be implemented into the surgical console 30 and/or the movable cart 60.

Each of the control tower 20, the surgical console 30, and the robotic arm 40 includes a respective computer 21, 31, 41. The computers 21, 31, 41 are interconnected to each other using any suitable communication network based on wired or wireless communication protocols.

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
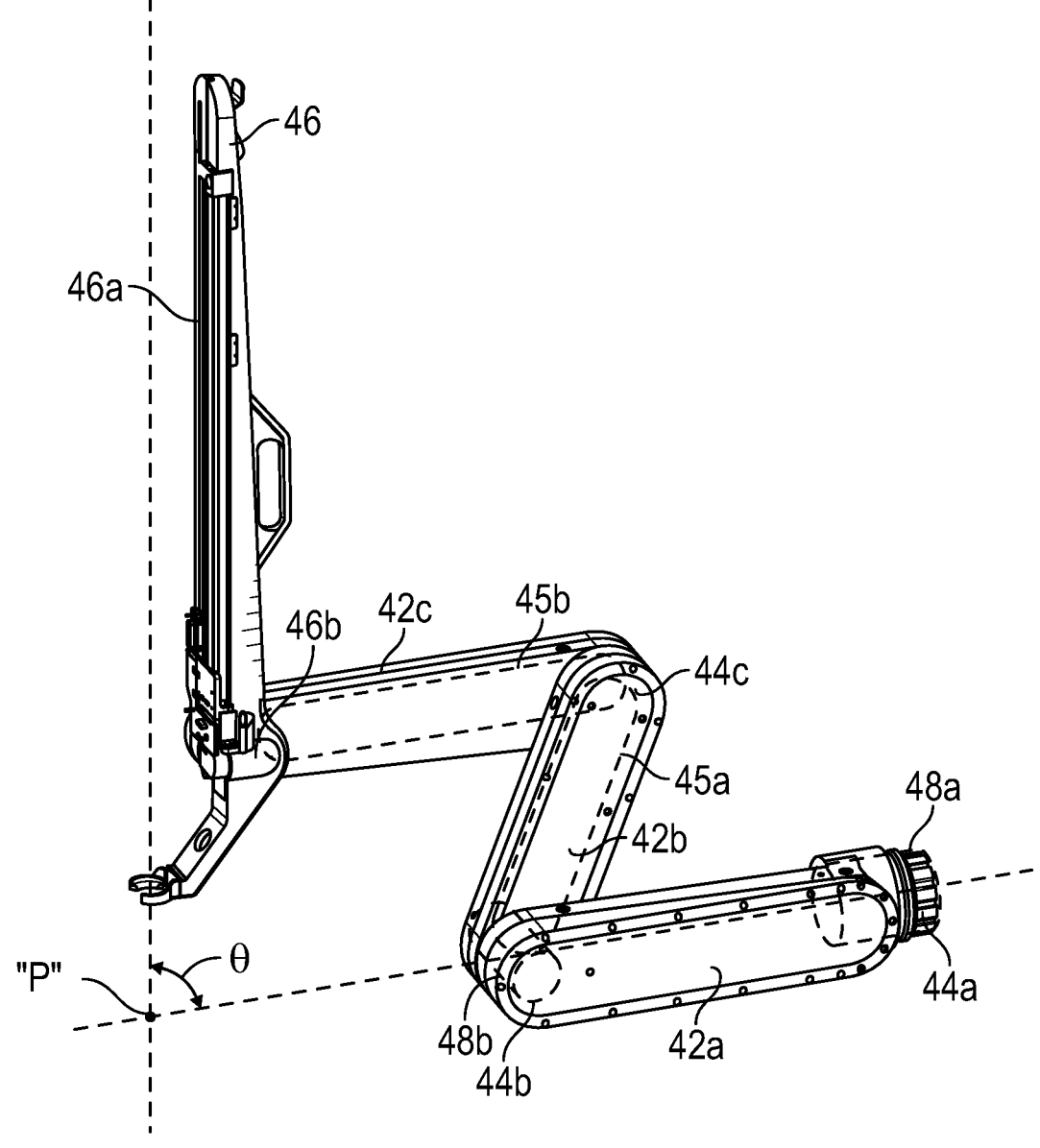
FIG. 2 is a perspective view of a surgical robotic arm of the surgical robotic system of FIG. 1.
Figure 3:
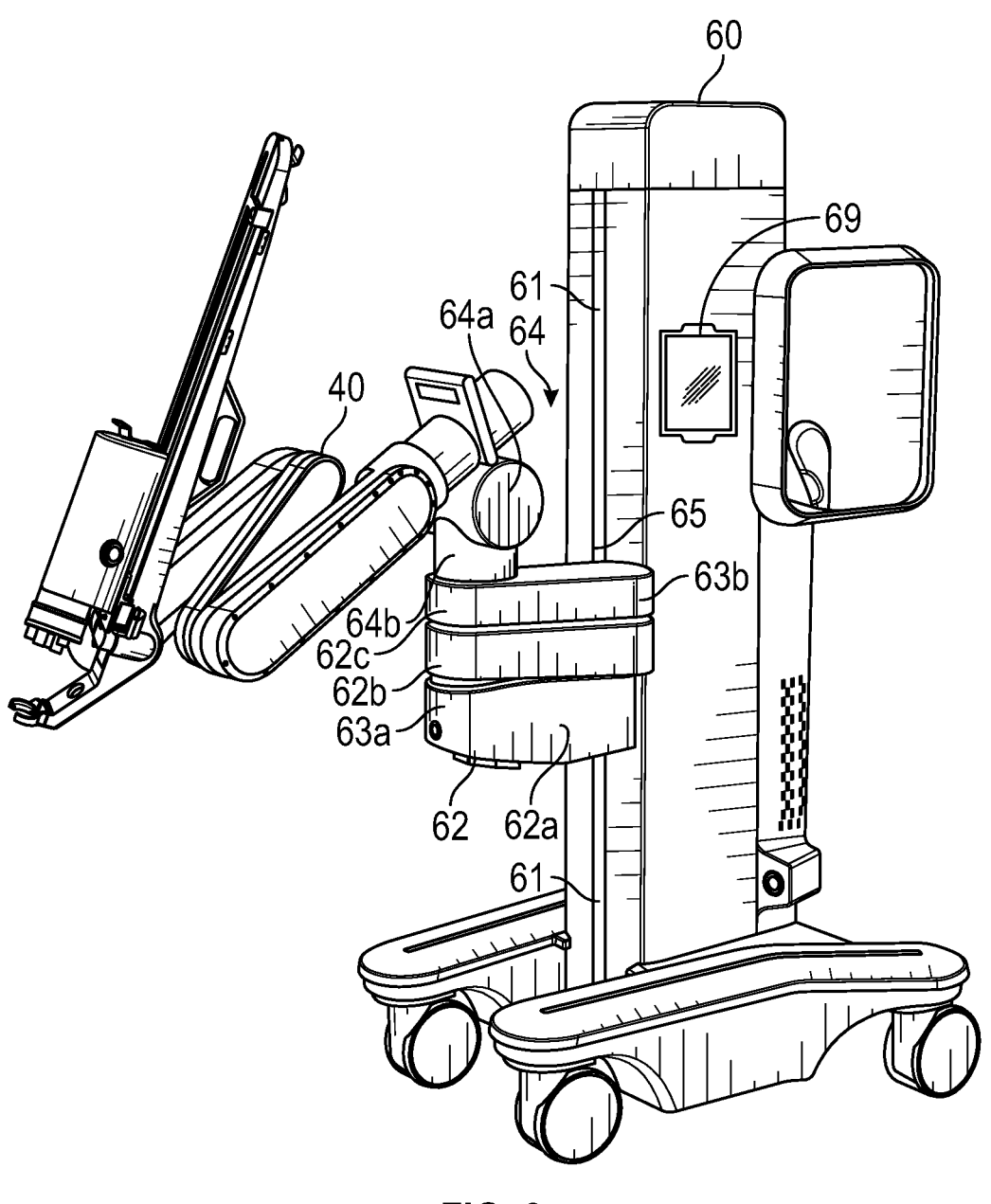
FIG. 3 is a perspective view of a setup arm with the surgical robotic arm of the surgical robotic system of FIG. 1.

With reference to FIG. 2, each of the robotic arms 40 may include a plurality of links 42*a*, 42*b*, 42*c*, which are interconnected at joints 44*a*, 44*b*, and 44*c*, respectively. The joint 44*a* is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*a* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In some instances, the robotic arm 40 may be coupled to the surgical table (not shown). The setup arm 62 includes controls 65 for adjusting movement of the links 62*a*, 62*b*, 62*c*, as well as the lift 61.

The third link 62*c* includes a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The robotic arm 40 also includes a plurality of manual override buttons 53 disposed on instrument drive unit 52 and the setup arm 62, which may be used in a manual mode. The user may press one or more of the buttons 53 to move the component associated with the button 53.

With reference to FIG. 2, the robotic arm 40 also includes a holder 46 defining a second longitudinal axis and configured to receive the instrument drive unit 52 (FIG. 1) of the surgical instrument 50, which is configured to couple to an actuation mechanism of the surgical instrument 50. Instrument drive unit 52 transfers actuation forces from its actuators to the surgical instrument 50 to actuate components (e.g., end effectors) of the surgical instrument 50. The holder 46 includes a sliding mechanism 46*a*, which is configured to move the instrument drive unit 52 along the second longitudinal axis defined by the holder 46. The holder 46 also includes a joint 46*b*, which rotates the holder 46 relative to the link 42*c*.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

The actuator 48*b* of the joint 44*b* is coupled to the joint 44*c* via the belt 45*a*, and the joint 44*c* is in turn coupled to the joint 46*c* via the belt 45*b*. Joint 44*c* may include a transfer case coupling the belts 45*a* and 45*b*, such that the actuator 48*b* is configured to rotate each of the links 42*b*, 42*c*, and the holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. Some or all of the joints 44*a*, 44*b*, and 44*c* may include an actuator to obviate the need for mechanical linkages.

Figure 4:
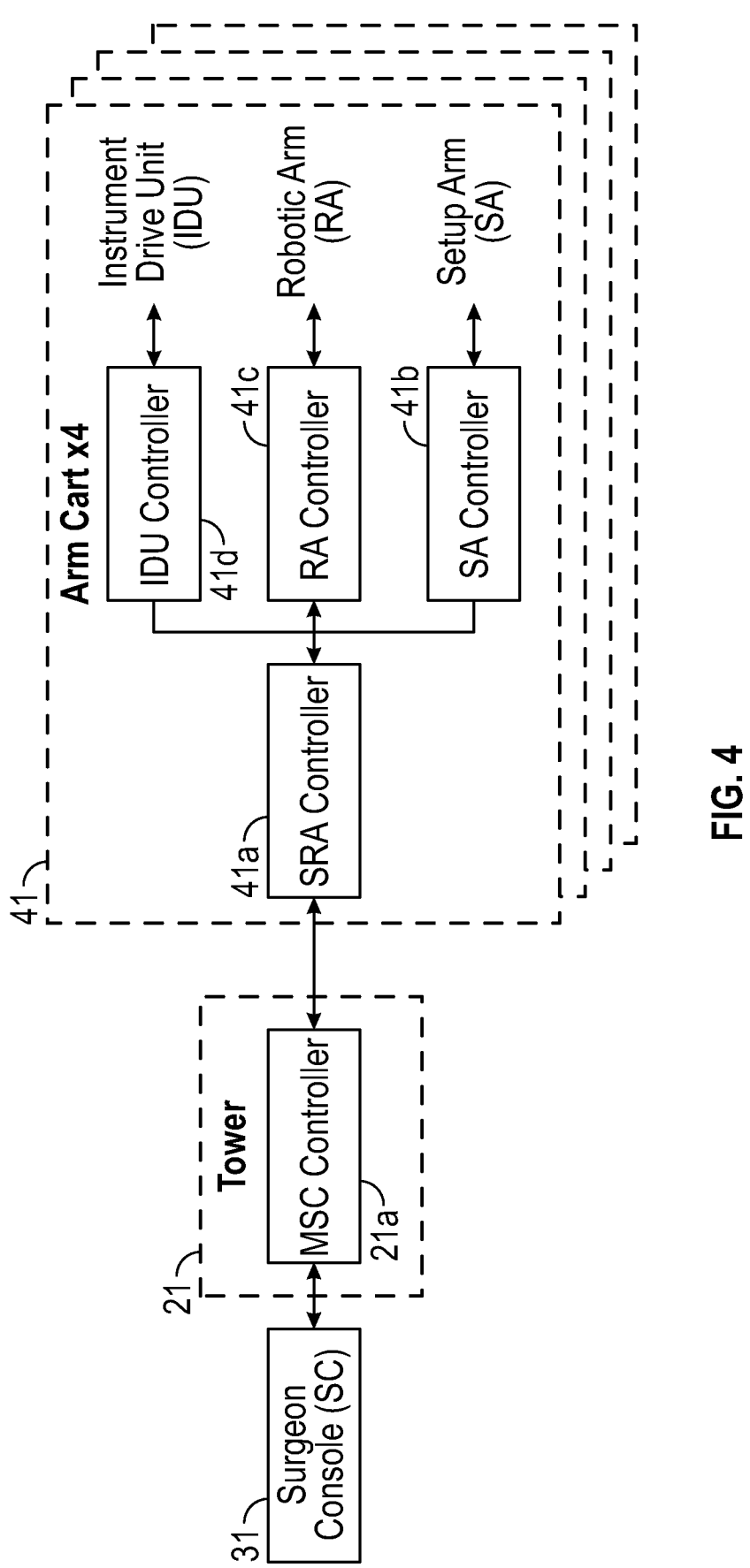
FIG. 4 is a schematic diagram of a computer architecture of the surgical robotic system of FIG. 1, including a surgical console.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgical console 30 about the current position and/or orientation of the handle controllers 38*a* and 38*b* and the state of the foot pedals 36 and other buttons. The controller 21*a* processes these input positions to determine desired drive commands for each joint of the robotic arm 40 and/or the instrument drive unit 52 and communicates these to the computer 41 of the robotic arm 40. The controller 21*a* also receives back the actual joint angles and uses this information to determine force feedback commands that are transmitted back to the computer 31 of the surgical console 30 to provide haptic feedback through the handle controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the movable cart 60, the robotic arm 40, and the instrument drive unit 52. The main cart controller 41*a* also communicates actual joint angles back to the controller 21*a*.

The setup arm controller 41*b* controls each of joints 63*a* and 63*b*, and the rotatable base 64 of the setup arm 62 and calculates desired motor movement commands (e.g., motor torque) for the pitch axis and controls the brakes. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the instrument drive unit 52. The IDU controller 41*d* calculates actual angles based on the motor positions and transmits the actual angles back to the main cart controller 41*a*.

The robotic arm 40 is controlled as follows. Initially, a pose of the handle controller controlling the robotic arm 40, e.g., the handle controller 38*a*, is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controller 38*a* may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38*a* is then scaled by a scaling function executed by the controller 21*a*. In some instances, the coordinate position may be scaled down and the orientation may be scaled up by the scaling function. In addition, the controller 21*a* also executes a clutching function, which disengages the handle controller 38*a* from the robotic arm 40. In particular, the main cart controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, and 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Figure 5:
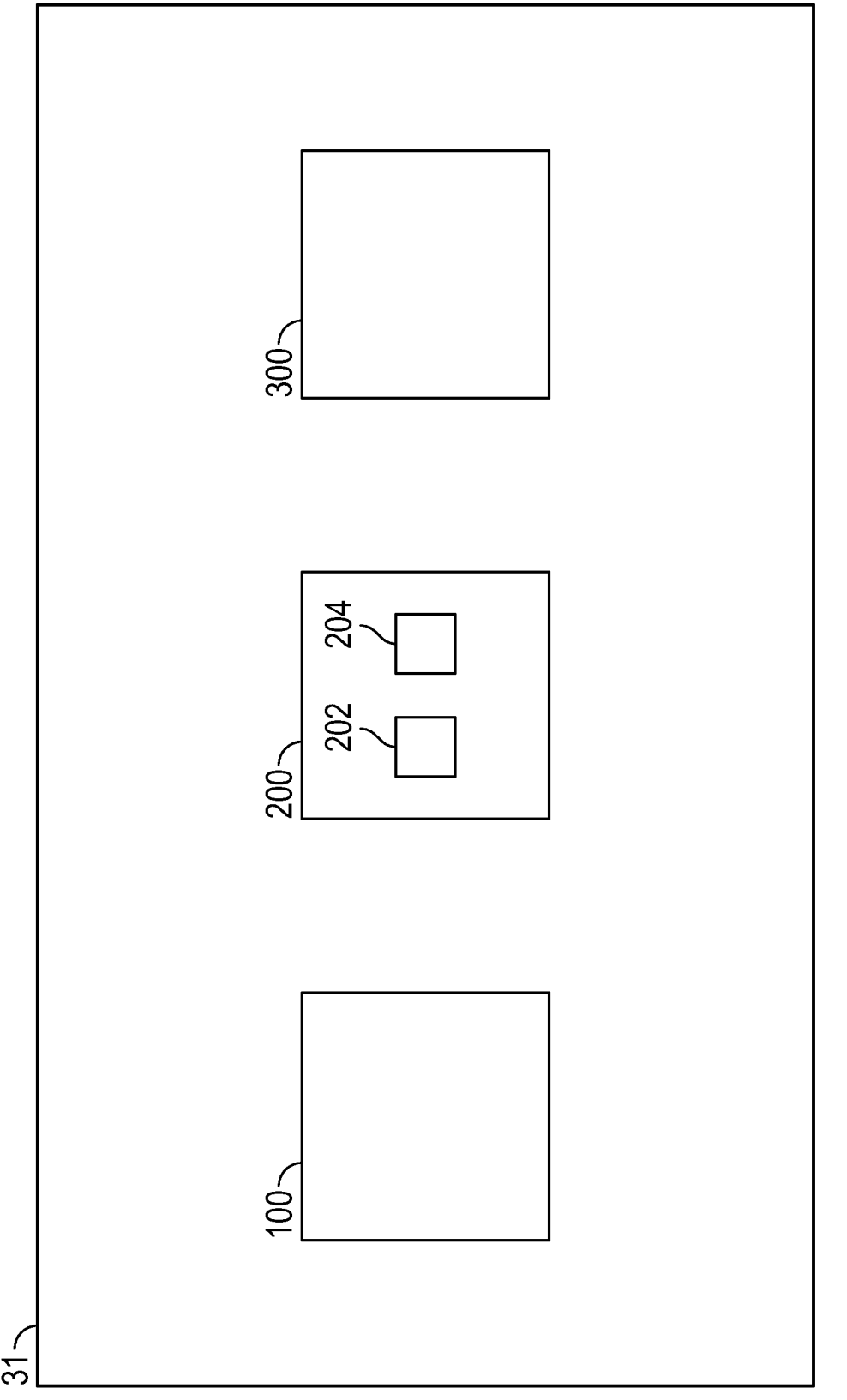
FIG. 5 is a schematic diagram of the surgical console of FIG. 4.

With continued reference to FIGS. 1, 4, and 5, the surgical console 30 further includes an image processor 100, a user interface controller 200, and memory 300. The user interface controller 200 is configured to receive input commands from the surgical console 30 via the handle controllers 38*a* and 38*b* and/or the foot pedals 36 and select user interface modes. In some instances, the surgical robotic system 10 may further include a microphone configured to receive a voice command from the clinician as the input command. The user interface modes include a first interface mode 202, a second interface mode 204, and a third interface mode. The user interface controller 200 may return to the previous user interface mode, in response to receiving an exit command as the input command. The user interface controller 200 may also deliver auditory or haptic feedback, based on the input commands, as confirmation of the user interface modes and/or exit command to the handle controllers 38*a* and 38*b* and/or the foot pedals 36.

With reference to FIG. 6, the first mode 202 is configured to display the video feed of the surgical site 310 provided by the camera 51 on the first display 32 and allow for control of the robotic arms 40 via the handle controllers 38*a* and 38*b* and/or the foot pedals 36.

Figure 7:
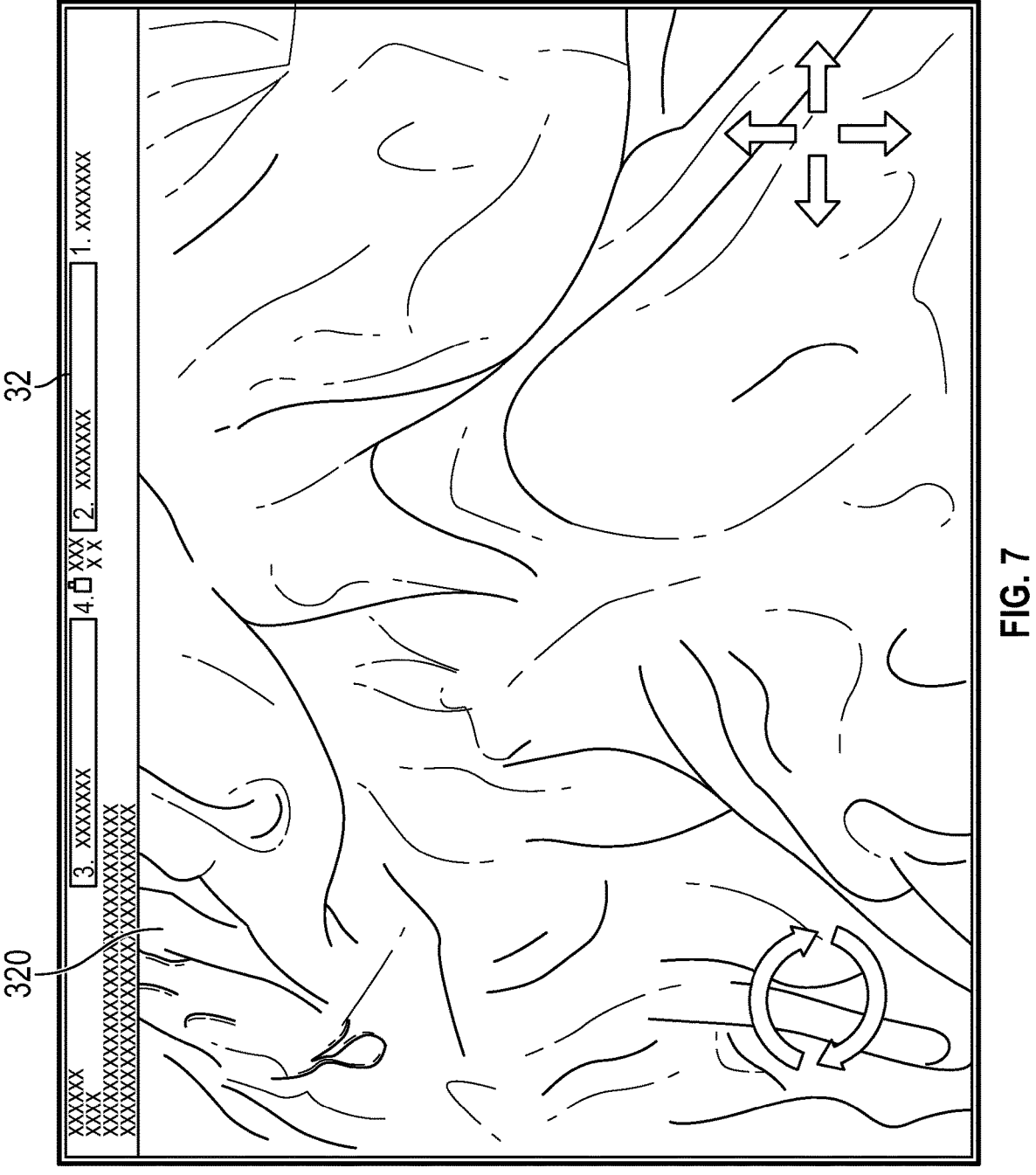
FIG. 7 is an exemplary view of a display of a 3D model of the target tissue, in a second mode.

With reference to FIG. 7, the second mode 204 is configured to display the 3D model 320 (of the target tissue/organ) on the first display 32 and allow for interactive control of the 3D model 320 via the handle controllers 38*a* and 38*b* and/or the foot pedals 36 to register the 3D model with the video feed. Interactive control of the 3D model 320 includes adjusting a scale, position, and/or orientation of the 3D model to match the scale, position and/or orientation of the target tissue (live or in-vivo) at the surgical site 310 in the video feed.

During the second mode 204, the interface controller 200 is further configured to maintain the actual position of the handle controllers 38*a* and 38*b* and/or the foot pedals 36 from the first interface mode 202, and sense a directional force on the handle controllers 38*a* and 38*b* and/or foot pedal 36 to determine a desired position, thereby allowing for seamless transition of the handle controllers 38*a* and 38*b* between the first interface mode 202 and the second interface mode 204. The interface controller 200 may be further configured to retain the actual position of the handle controllers 38*a* and 38*b* and/or the foot pedal 36 from the first interface mode 202, and allow for further movement of the the handle controllers 38*a* and 38*b* and/or the foot pedal 36. As such, when the interface controller 200 switches back to the first interface mode 202 from the second interface mode 204, the retained actual position of the handle controllers 38*a* and 38*b* and/or the foot pedal 36 are used to return the handle controllers 38*a* and 38*b* and/or the foot pedal 36 position to the retained actual position prior to movement of the handle controllers 38*a* and 38*b* and/or the foot pedal 36 in the second interface mode 204.

The image processor 100 is configured to receive the pre-operative 3D model 320 (FIG. 7) of a target tissue at the surgical site 310 (FIG. 6) from memory 300 based on preoperative diagnostic images taken of the target tissue at the surgical site 310 (e.g., CT, MRI, fluoroscopic imaging). The 3D model 320 may be reconstructed using any suitable method to generate different 3D model 320 rendering such as, surface, voxel, and/or cutaway. Other suitable methods for generating 3D models 320 from the preoperative diagnostic images are also contemplated. The image processor 100 may store the 3D model 320 and the various renderings of the 3D model 320 in memory 300.

The image processor 100 is further configured to analyze the surface of the target tissue at the surgical site 310 by determining at least one of tissue property, mechanical property, and/or shape of the target tissue at the surgical site 310. The tissue properties and mechanical properties may include, for example, insufflation, age of tissue, thickness of tissue, gravity acting on the tissue, perfusion, vascularity, etc. Based on the determined tissue properties, mechanical properties, and/or shape of the target tissue, the image processor 100 further manipulates the 3D model 320 to register the 3D model 320 to the target tissue at the surgical site 310.

In some instances, memory 300 may store virtual containers corresponding to mathematical rules that replicate the effects of the mechanical properties acting on the in-vivo target tissue at the surgical site 310, and the image processor 100 applies the virtual containers to the 3D model 320 to assist in manipulation of the 3D model 320 consistent with the in-vivo target tissue at the surgical site 310.

Additionally, and/or alternatively, the image processor 100 may identify fiducial markings disposed on the in-vivo target tissue (or which form a part of the target tissue) at the surgical site 310 and/or on the 3D model 320 to assist with registration of the 3D model 320 to the in-vivo target tissue at the surgical site 310 by matching the fiducial markings of the in-vivo target tissue with the fiducial markings of the 3D model 320. The image processor 100 may be configured to generate additional 3D models based on the in-vivo video feed to further assist with manipulating the 3D model 320 to register the 3D model 320 to the target tissue at the surgical site 310.

The image processor 100 is further configured to indicate the progress of the registration of the 3D model 320 with the target tissue at the surgical site 310 based on a proportionate volume registered between the surface of the manipulated 3D model 320 and the target tissue at the surgical site 310.

Figure 8:
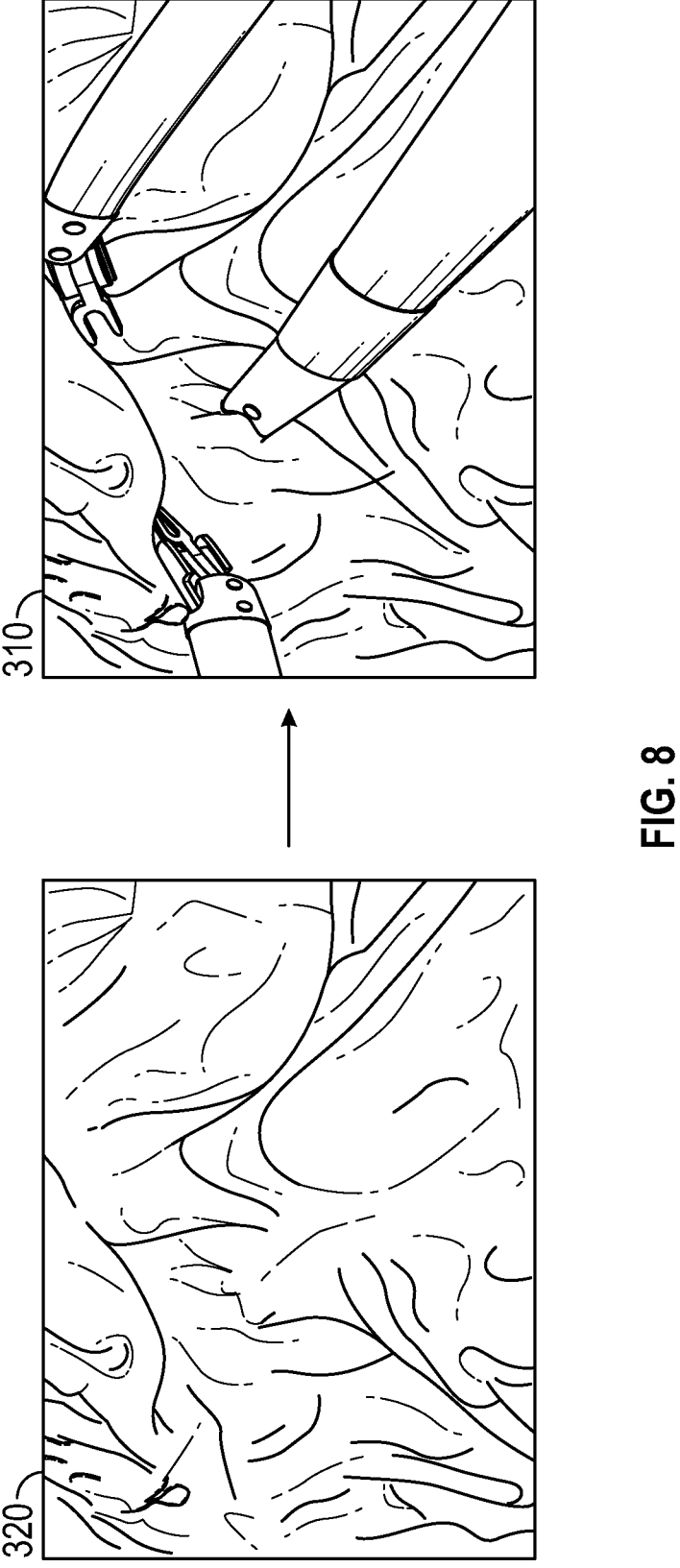
FIG. 8 is an exemplary view of the 3D model of the target tissue superimposed on the display of the target tissue at the surgical site.

With reference to FIG. 8, once registration is complete, the interface controller 200 switches to the third interface mode, in which the image processor 100 superimposes the target tissue at the surgical site 310 over the 3D model 320 to create an augmented view and the handle controllers 38a and 38b and/or the foot pedals are used by the clinician to continue operation via teleoperation of the robotic arms 40 via the surgical console. The image processor 100 is configured to control the transparency of the 3D model 320 in the augmented view. The level of transparency of the 3D model 320 in the augmented view is controlled via the handle controllers 38a and 38b. The image processor 100 is further configured to synchronize a viewpoint of the 3D model 320 with a position and/or orientation of the camera 51 of the in-vivo target tissue at the surgical site 310 in the in-vivo video feed. Thus, when the position and/or orientation of the camera 51 is adjusted, e.g., panning up or down, rotating, and/or zooming in or out, the adjusted position and/or orientation is translated into a corresponding viewpoint of the 3D model 320 to maintain registration with the target tissue at the surgical site 310.

Figure 9:
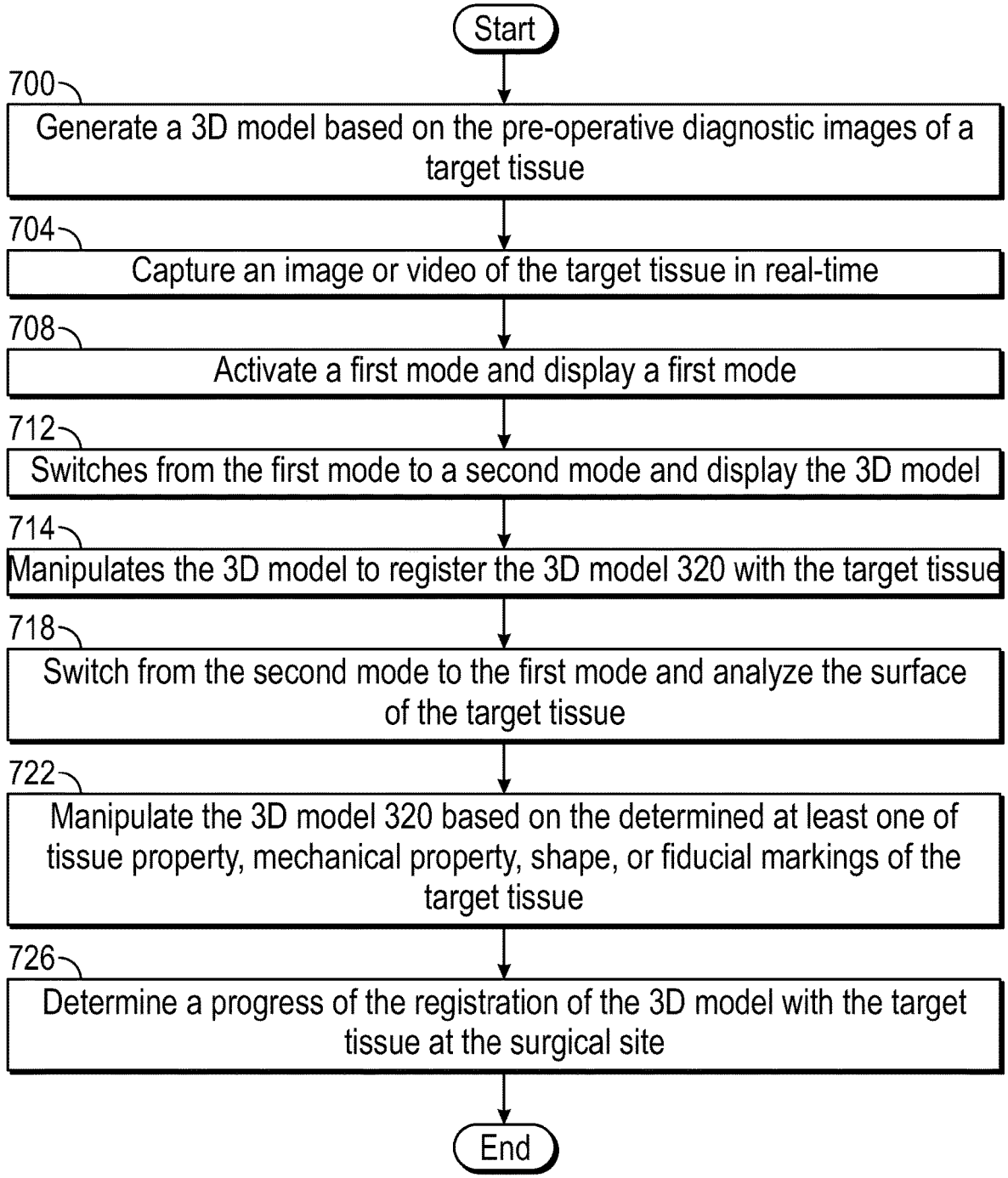
FIG. 9 is a flow chart of a method according to the present disclosure for registration of a 3D model with a target tissue of the surgical site through integrated control of a 3D visualization.

With reference to FIG. 9, in operation, at step 700, the image processor 100 generates a 3D model 320 based on the pre-operative diagnostic images taken prior to the procedure of a target tissue at the surgical site 310. At step 704, camera

51, disposed on the robotic arm 40, captures an image or video of the target tissue in real-time. At step 708, the surgical robotic system 10 activates a first mode 202 to display the target tissue in real-time and allow treatment of the target tissue in response to the handle controllers 38a and 38b and/or the foot pedals 36. Upon displaying the video feed of the surgical site 310 on the first display 32, the user interface controller 200 activates remote control of the robotic arms 40, e.g., teleoperation of the robotic arms 40 via foot pedals 36 and/or handle controllers 38a, 38b on the surgical console 30. The clinician teleoperates the robotic arms 40 to perform the surgical operation.

At step 712, the user interface controller 200 switches from the first mode 202 to the second mode 204 to display the 3D model 320. In switching from the first mode 202 to the second mode 204, the user interface controller 200 receives an exit command via the handle controllers 38a and 38b and/or the foot pedals 36, or in some instances voice command. The robotic surgical system 10 exits the first mode 202 and deactivates the remote control of the robotic arms 40. In some instances, the user interface mode may be switched to the second mode 204, the previous mode, or the non-selected mode. Once the second mode 204 is selected, the user interface controller 200 displays the 3D model 320 of the target tissue on the first display 32. Upon displaying the 3D model 320, the user interface controller 200 activates interactive control of the 3D model 320 on the first display 32 via the handle controllers 38a and 38b and/or the foot pedals 36 on the surgical console 30.

The clinician, in step 714, manipulates the 3D model 320, via the handle controllers 38a and 38b and/or the foot pedals 36, to register the 3D model 320 with the target tissue. The 3D model 320 is manipulated by allowing interactive control of the 3D model 320 via foot pedals 36 and/or handle controllers 38a, 38b to adjust at least one of a scale, position, and/or orientation of the 3D model 320 (as indicated by the arrows of FIGS. 7 and 8). At step 718, the interface controller 200 switches from the second mode 204 to the first mode 202, and the image processor 100 analyzes the surface of the target tissue and determines at least one of tissue property, mechanical property, shape, or fiducial markings of the target tissue.

Additionally, it is contemplated that the 3D model 320 may be generated and/or manipulated/controlled by foot pedals 36 and/or handle controllers 38a and 38b taking into account or incorporating heuristic computational model controls, methods, and/or techniques. Generally, heuristics are methods for solving problems in a quick way that delivers a result that is sufficient enough to be useful given the time constraints.

By way of non-limiting example, the 3D model 320, that is generated, may be adjusted, via the handle controllers 38a and 38b or the like, to take into consideration at least some or all of the following factors (i.e., heuristic factor): age of the patient, gender of the patient, height of the patient, weight of the patient, orientation of the patient on the surgical table, effects of gravity based on patent orientation, time/duration spent in the orientation, hydration of the patient/organ, density of the organ, temperature of the patient/organ, respiration rate of the patent, blood pressure, body mass index (BMI) of the patient, percentage of abdominal fat, percentage of vascularity of the organ. Numerical values for each of these factors may be measured, observed, calculated or otherwise obtained, and these numerical values may be added to the 3D model 320, taking into consideration the heuristic factors, either during generation thereof, and/or may be used during control of the 3D model 320 via the foot pedals 36 and/or handle controllers 38*a* and 38*b*.

At step 722, based on the determined at least one of tissue property, mechanical property, shape, or fiducial markings of the target tissue the 3D model 320 is further manipulated to register the 3D model 320 with the target tissue. At step 726, the image processor 100 compares the surface volume of the 3D model 320 to the surface volume of the target tissue to determine the progress of the registration of the 3D model 320 with the target tissue at the surgical site 310. Upon competition of the registration of the 3D model 320 with the target tissue in real-time, at step 730, the 3D model 320 is superimposed over the in-vivo target tissue at the surgical site 310 to create an augmented view (FIG. 8). In maintaining registration of the 3D model 320 with the in-vivo target tissue at the surgical site 310 at least one of a position or orientation of the camera 51 is synchronized with a viewpoint of the 3D model 320. Further, the surgical robotic system 10 switches from the second mode 204 to the first mode 202, to display the augmented view and activate remote control of the robotic arms 40, e.g., teleoperation of the robotic arms 40 via foot pedals 36 and/or handle controllers 38*a*, 38*b* on the surgical console 30.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical robotic system comprising:
a control tower;
a mobile cart coupled to the control tower, the mobile cart including a surgical robotic arm, the surgical robotic arm including:

a surgical instrument actuatable in response to a user input and configured to treat a target tissue in real-time; and
   an image capture device configured to capture at least one of images or video of the target tissue in real-time;
a surgical console coupled to the control tower, the surgical console including:
   a display;
   a memory configured to store pre-operative images of the target tissue;
   a user input device configured to generate the user input; and
   a controller operably coupled to the display, the memory, and the user input device, the controller configured to switch, based on the user input, from a first mode to a second mode, and from the second mode to the first mode,
wherein the first mode includes displaying the target tissue in real-time in the at least one of images or video on the display and activating control of the surgical robotic arm by the user input device, and the second mode includes superimposing a 3D model of the target tissue over the target tissue in the at least one of images or video, activating interactive control of the 3D model of the target tissue by the user input device, and registering the 3D model of the target tissue with the target tissue in the at least one of images or video, wherein the controller is further configured to determine completion of the registration of the 3D model with the target tissue and switch from the second mode to the first mode in response to the completion of the registration.

2. The surgical robotic system according to claim 1, wherein the surgical console further includes an image processor configured to generate the 3D model of the target tissue based on the stored pre-operative images of the target tissue at the surgical site.

3. The surgical robotic system according to claim 1, wherein the interactive control of the 3D model of the target tissue includes adjusting at least one of scale, position, orientation of the 3D model of the target tissue or at least one heuristic factor.

4. The surgical robotic system according to claim 1, wherein in switching from the first mode to the second mode, the controller is further configured to maintain or retain an actual position of the user input device from the first mode.

5. The surgical robotic system according to claim 4, wherein in maintaining the actual position of the user input device from the first mode, the controller is further configured to determine a desired position of the user input device by sensing a directional force on the user input device.

6. The surgical robotic system according to claim 1, wherein in switching from the second mode to the first mode, the controller is further configured to analyze the surface of the target tissue in real-time.

7. The surgical robotic system according to claim 6, wherein when analyzing the surface of the target tissue in real-time, the controller is further configured to determine at least one of tissue property, mechanical property, shape, or fiducial markings of the target tissue.

8. The surgical robotic system according to claim 7, wherein the controller is further configured to manipulate the 3D model of the target tissue based on the determined at least one of tissue property, mechanical property, shape, fiducial markings of the target tissue in real-time or heuristic factors to further register the 3D model of the target tissue with the target tissue in real-time.

9. The surgical robotic system according to claim 1, wherein the controller is further configured to determine completion of registration of the 3D model of the target tissue with the target tissue in real-time.

10. The surgical robotic system according to claim 9, wherein the controller is further configured to superimpose the 3D model of the target tissue over the target tissue in real-time, based on the completion of registration of the 3D model of the target tissue with the target tissue in real time.

11. The surgical robotic system according to claim 10, wherein the controller is further configured to synchronize at least one of a position or orientation of the image capture device with a viewpoint of the 3D model of the target tissue.

12. A method of registering a 3D model of a target tissue with a real-time image of the target tissue via a user input device of a surgical robotic system, the method comprising:
   generating a 3D model of a target tissue based on stored pre-operative images of the target tissue;
   capturing, by an image capture device, at least one of images or video of the target tissue in real-time;
   activating a first mode to display the target tissue in real-time in the at least one of images or video on the display and treat the target tissue in response to a user input device;
   switching from the first mode to a second mode to superimpose the 3D model of the target tissue over the target tissue in the at least one of images or video;
   manipulating the 3D model, via the user input device, to register the 3D model of the target tissue with the target tissue in real-time in the at least one of images or video;
   determining completion of the registration of the 3D model with the target tissue; and
   switching from the second mode to the first mode in response to the completion of the registration.

13. The method according to claim 12, wherein manipulating the 3D model of the target tissue to register the 3D model of the target tissue with the target tissue in real-time includes activating interactive control of the 3D model of the target tissue via the user input device.

14. The method according to claim 13, wherein the interactive control of the 3D model of the target tissue includes adjusting at least one of scale, position, orientation of the 3D model of the target tissue or heuristic factors.

15. The method according to claim 12, wherein switching from the first mode to the second mode includes maintaining an actual position of the user input device and sensing a directional force on the user input device to determine a desired position of the user input device.

16. The method according to claim 12, wherein switching from the second mode to the first mode to further register the 3D model of the target tissue with the target tissue includes analyzing the surface of the target tissue in real-time.

17. The method according to claim 16, wherein analyzing the surface of the target tissue in real-time includes determining at least one of tissue property, mechanical property, shape, or fiducial markings of the target tissue in real-time.

18. The method according to claim 17, wherein determining the at least one of tissue property, mechanical property, shape or fiducial markings of the target tissue in real-time includes manipulating the 3D model of the target tissue based on the determined at least one of tissue property, mechanical property, shape, fiducial markings of the target tissue in real-time or heuristic factors.

19. The method according to claim 12, further comprising:
   determining completion of registration of the 3D model of the target tissue with the target tissue in real-time; and
   superimposing the 3D model of the target tissue over the target tissue in real-time, based on the completion of the registration of the 3D model of the target tissue with the target tissue in real-time.

20. The method according to claim 19, further comprising:
   synchronizing at least one of a position or orientation of the image capture device with a viewpoint of the 3D model of the target tissue.

* * * * *